US005672622A

United States Patent [19]
Hedgepeth et al.

[11] Patent Number: 5,672,622
[45] Date of Patent: Sep. 30, 1997

[54] TREATMENT OF MULTIPLE SCLEROSIS

[75] Inventors: Joseph Hedgepeth, San Francisco, Calif.; Helmut Wachtel, Berlin, Germany

[73] Assignee: Berlex Laboratories, Inc., Richmond, Calif.

[21] Appl. No.: 327,478

[22] Filed: Oct. 21, 1994

Related U.S. Application Data

[63] Continuation of Ser. No. 231,969, Apr. 21, 1994, abandoned.

[51] Int. Cl.$^6$ ....................................................... A61K 31/40
[52] U.S. Cl. .......................... 514/424; 514/258; 514/392; 548/543
[58] Field of Search ................................. 548/551, 543; 514/424, 258, 392

[56] References Cited

U.S. PATENT DOCUMENTS

| | | | |
|---|---|---|---|
| 4,153,713 | 5/1979 | Huth et al. | 424/274 |
| 4,943,573 | 9/1993 | Meanwell et al. | 514/253 |
| 5,227,369 | 7/1993 | Rosen et al. | 514/23 |
| 5,420,154 | 5/1995 | Christansen IV et al. | 514/424 |
| 5,541,219 | 7/1996 | Fenton et al. | 514/432 |

FOREIGN PATENT DOCUMENTS

| | | |
|---|---|---|
| 0 411 754 | 2/1991 | European Pat. Off. |
| 92/02220 | 2/1992 | WIPO |
| 92/19594 | 11/1992 | WIPO |
| 93/16706 | 9/1993 | WIPO |
| 93/19068 | 9/1993 | WIPO |

OTHER PUBLICATIONS

"Differential modulation of tissue function and therapeutic potential of selective inhibitors of cyclic nucleotide phosphodiesterase isoenzymes", C.D. Nicholson et al., *TiPS*, vol. 12, Jan. 1991.

"Inhibition of Eosinophil Oxygen Radical Production by Type IV—But Not Type III—Selective cAMP Phosphodiesterase Inhibitors", G. Dent et al., *Br. J. Pharm.*, vol. 22, (163P), 1990.

"Demyelinating Diseases", Cecil Textbook of Medicine, Wyngaarden et al., eds., 19th ed., 1992, pp. 2199–2200.

"Pentoxifylline inhibits experimental allergic encephalomyelitis", S. Nataf et al., *Acta Neurol. Scand.*, vol. 88, 1993, pp. 97–99.

"Regulation of Tumor Necrosis Factor Expression in macrophage-like Cell Line by Lipopolysaccharide and cyclic AMP", S.M. Taffet et al., *Cellular immunology*, vol. 120, 1989, pp. 291–300.

"The identification of a new cyclic nucleotide phosphodiesterase activity in human and guinea-pig cardiac ventricle", M.L. Reeves et al., *Biochem J.*, vol. 241, 1987, pp. 535–541.

"Phosphodiesterase inhibitor pentoxifylline, a selective suppressor of T helper type 1—but not type 2—associated lymphokine production, prevents induction of experimental autoimmune encephalomyelitis in Lewis rats", O. Rott et al., *Eur. J. Immunol.*, vol. 23, 1993, pp. 1745–1751.

"The specific type III and IV phosphodiesterase inhibitor zardaverine suppresses formation of tumor necrosis factor by macrophages", F.U. Schade and C. Schudt, *Eur. J. Pharma.*, vol. 230, 1993, pp. 9–14.

"Multiple Sclerosis and Allied Demyelinative Diseases", *Principles of Neurology*, 1993, pp. 777–791.

Molnar–Kimber et al., *Mediators of Inflammation*, "Differential regulation of TNF$\alpha$ and II–1$\beta$ production from endotoxin stimulated human monocytes by phosphodiesterase inhibitors" (1992).

Sharief et al., "Association Between Tumor Necrosis Factor–alpha . . .," *new England J. of Med.*, 325(7):467–472, Aug. 15, 1991.

Benvenuto et al., "Increased Synthesis of Tumor Necrosis Factor . . .," *J. Neurol.*, 237(SUP1):83, 1990.

Kirby et al., "Prostacyclin Increases Cyclic–Nucleotide . . . ," *The Lancet*, 2(8192):453–454, Aug. 30, 1980.

Renz et al., "Release of Tumor Necrosis Factor–$\alpha$From Macrophages . . . ," *J. of Immunology*, pp. 2388–2393, Oct. 1, 1988.

Strieter et al., "Cellular and Molecular Regulation of Tumor . . . ," *Biochem. and Biophys. Research Comm.*, 155(3):1230–1236, Sep. 30, 1988.

Spengler et al., "Dynamics of Cyclic AMP– and Prostaglandin . . . ," *Infectionand Immunity*, 57(9):2837–2841, Sep. 1989.

Lloyd J. Old, "Tumor necrosis factor: Another chapter in the long . . . ," *Nature*, vol. 330, pp. 602–603, Dec. 17, 1987.

Miller et al., "Tumour Necrosis Factor in Bronchopulmonary . . . ," *Lancet*, vol. II for 1989, pp. 712–714, Sep. 23, 1989.

Tracey et al., "Anti–cachectin/TNF monoclonal antibodies prevent . . . ," *Nature*, vol. 330, pp. 662–664, Dec. 17, 1987.

Dezube et al., "Pentoxifylline and wellbeing in patients with cancer," *Lancet*, 335 (8690):662, Mar. 17, 1990.

Frölich et al., "In the Elevation of Cyclic . . . ," *J. Invest. Dermat.*, 90(2):240, 1988.

Marivet et al., "Inhibition of Cyclic Adenosine-3', 5'-monophosphate . . . ," *J., Med. Chem.*, 32:1450–1457, 1989.

*Primary Examiner*—Richard L. Raymond
*Attorney, Agent, or Firm*—Millen, White, Zelano & Branigan, P.C.

[57] ABSTRACT

The present invention is a method of preventing or ameliorating the episodic recurrence of MS, comprising administering an effective amount of selective phosphodiesterase inhibitors of Type IV, e.g., Rolipram, e.g., wherein the severity of the episodic recurrences is ameliorated or the time period between episodes is lengthened.

32 Claims, 2 Drawing Sheets

TREATMENT OF MULTIPLE SCLEROSIS

BACKGROUND OF THE INVENTION

This is a continuation of application Ser. No. 08/231,969, filed Apr. 21, 1994 now abandoned.

Demyelinating diseases are severe afflictions of the brain and spinal cord, involving the destruction of the myelin sheath which surrounds nerve fibers. As a result of demyelination, various neurological symptoms are manifested, including motor impairment, visual loss, and sensory changes. Multiple sclerosis (MS) is the most common of the demyelinating diseases. It is a disease characterized by episodes of focal disorder of the optic nerves, spinal cord, and brain. Typically, it produces recurring episodes of neurologic dysfunction, followed by remission (relapsing-remitting), but it may also be chronic. Although MS is a well-studied disease, its precise cause remains undetermined.

At present, there is no method for preventing MS. See Cecil's Textbook of Medicine (Wyngaarden, 1993). Until recently, treatments have been empirical and not entirely successful. For example, adrenocortical hormone (ACTH), methylprednisone, and prednisone have been shown to have a beneficial effect on the disease. However, a large number of patients do not respond to such treatment. Moreover, there is no evidence that ACTH and steroids have an effect on the ultimate course of the disease or that they prevent its recurrence. Additionally, amantadine, baclofen, and diazepam have been administered. Recently, Betaseron® (Berlex Laboratories, Inc., Wayne, N.J.) has been approved for the clinical treatment of patients having relapsing-remitting MS. It is, therefore, evident that a variety of approaches have been used to treat MS, targeting different physiological and cellular components. For a review of treatments, e.g., see Principles of Neurology, Fifth Edition, (Adams et al., 1993). There remains a need for additional drugs which have an effect on the disease's severity and progression.

SUMMARY OF THE INVENTION

The present invention relates to a method of treating or preventing MS, comprising administering an effective amount of, e.g., a 2-pyrrolidone compound, e.g., of formula I below, preferably Rolipram, a Type IV phosphodiesterase.

The invention, in one aspect, relates to racemates and optically active 4-(polyalkoxyphenyl)-2-pyrrolidones of formula I which are useful in preventing or treating multiple sclerosis:

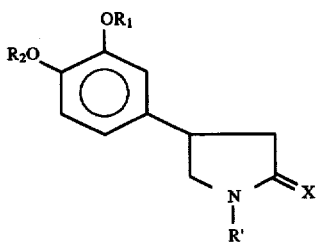

wherein $R_1$ and $R_2$ each are alike or different and are hydrocarbon of up to 18 carbon atoms with at least one being other than methyl, a heterocyclic ring, or alkyl of 1–5 carbon atoms which is substituted by one or more of halogen atoms, hydroxy, carboxy, alkoxy, alkoxycarbonyl or an amino group; R' is a hydrogen atom, alkyl, aryl or acyl; and X is an oxygen atom or a sulfur atom.

These compounds and the methods of making them are described, e.g., in U.S. Pat. No. 4,193,926 and WO 92/02220.

A preferred compound according to the present invention is Rolipram. Rolipram is 4-[(3-cyclopentyloxy)-4-methoxyphenyl]-2-pyrrolidinone. See, e.g., Merck Index, 11th edition, pages 1312–1313. It is commercially available from Schering AG, Berlin, Germany, or may be prepared, e.g., according to Belgian Patent No. 826,923 or U.S. Pat. No. 4,193,926. It is useful conventionally as an antidepressant, e.g., U. Schwabe et al., Mol. Pharmacol. 12, 900 (1976); H. Wachtel, Neuropharmacol. 22, 267 (1983); H. Wachtel and H. Schneider, Neuropharmacol. 25, 1119 (1986); W. Krause and G. Kühne, Xenobiotica 18, 561 (1988). Clinical evaluation of Rolipram for depression is reported in E. Zeller et al., Pharmacopsychiatry 17, 188 (1984). A comparative clinical trial with amitriptyline, q.v. in severe depressions is reported in F. Eckmann et al., Curr. Ther. Res. 43, 291 (1988). Derivatives of Rolipram can also be used according to the invention, i.e., compounds which are structurally related to Rolipram, and are effective in preventing and/or treating MS, e.g., those of formula I.

The present invention generally relates to the use of a Type IV phosphodiesterase inhibitor, preferably a compound of formula I, especially Rolipram, in multiple sclerosis (MS), for preventing, and/or ameliorating the severity, symptoms, and/or periodicity of recurrence of the disease, e.g., lengthening the time period between episodes in which symptoms flare, and/or suppressing the ongoing immune or autoimmune response associated with the disease.

The invention thus relates to the administration of an effective amount of such a compound, e.g., one according to formula I, preferably Rolipram, to a patient to prevent or treat MS. The amount of said compound, e.g., Rolipram, administered is an amount which is effective, for example, in preventing or ameliorating the symptoms of the disease or the disease's recurrence, or affecting the ultimate course of the disease, e.g., blocking the inflammatory response in the brain, the appearance of inflammatory lesions, neuronal or neuroglia cell death, and/or demyelination and the symptoms typically associated with pathogenesis of the disease.

The present invention also provides pharmaceutical compositions comprising a compound according to formula I, preferably a Type IV phosphodiesterase inhibitor, preferably Rolipram, which are useful in preventing or treating multiple sclerosis. According to the method, a compound can be administered, e.g., in a single dose, in multiple doses, e.g., through-the-skin injection or by sustained release means such as an implanted osmotic pump.

Upon further study of the specification and appended claims, further objects and advantages of this invention will become apparent to those skilled in the art.

BRIEF DESCRIPTION OF THE DRAWINGS

Various other objects, features, and attendant advantages of the present invention will be more fully appreciated as the same becomes better understood, when considered in conjunction with the accompanying drawings, in which like reference characters designate the same or similar parts throughout the several views and wherein.

Figure 1:
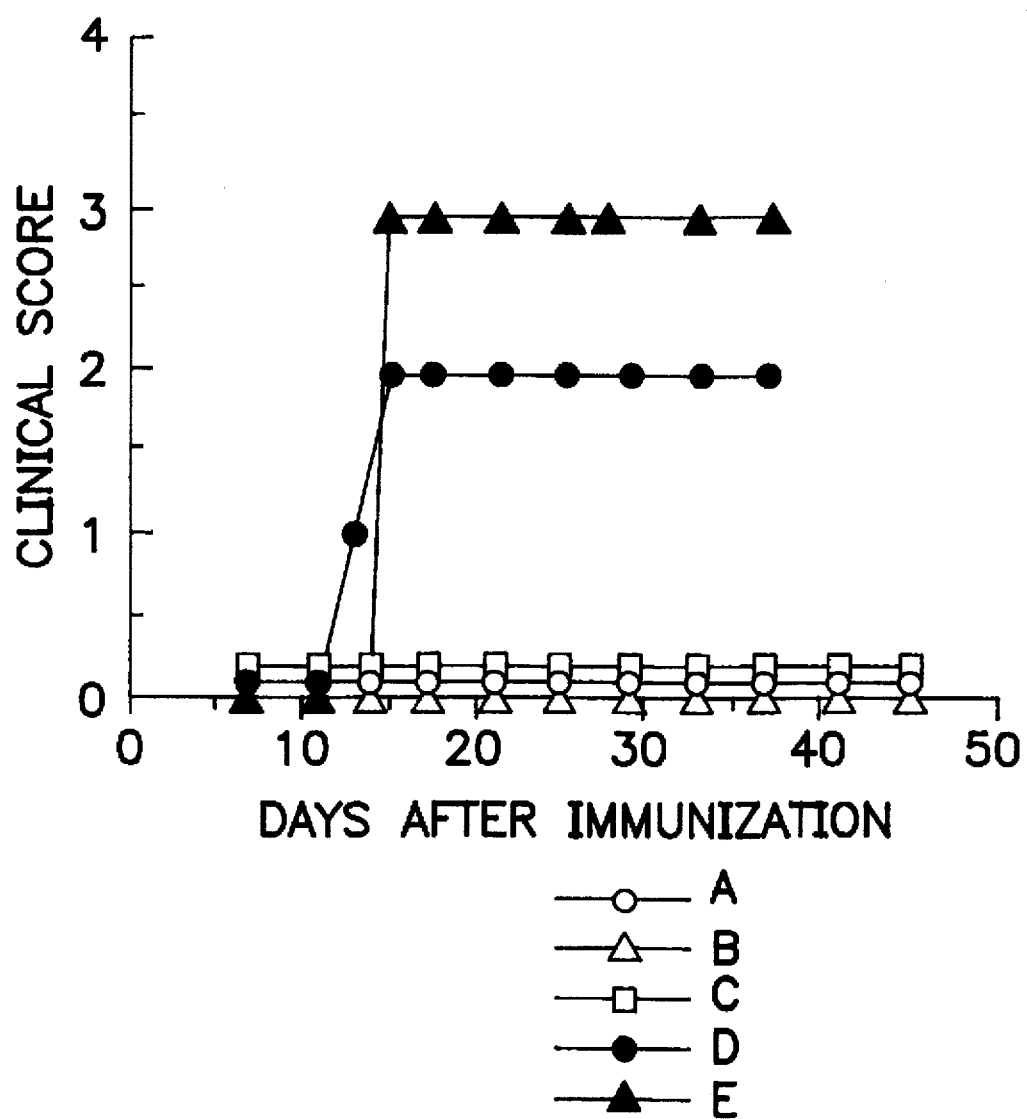
FIG. 1 shows the prevention of Experimental Allergic Encephalomyelitis (EAE) by Rolipram in a marmoset. A, B, and C received Rolipram (10 mg/kg) in DMSO; D and E received an equivalent volume of DMSO. Marmosets immunized with human spinal cord homogenerate received either Rolipram or placebo five days after immunization.

According to the present invention, a pharmaceutical composition comprising an effective amount of a compound described above can be administered to patients having multiple sclerosis, e.g., multiple sclerosis variants such as Neuromyelitis Optica (Devic's Disease), Diffuse Sclerosis, Transitional Sclerosis, Acute Disseminated Encephalomyelitis, and Optic Neuritis.

Symptoms of MS which are prevented or ameliorated or treated include: weakness and/or numbness in one or more limbs; tingling of the extremities and tight band-like sensations around the trunk or limbs; dragging or poor control of one or both legs to spastic or ataxic parepesis; hyperactive tendon reflexes; disappearance of abdominal reflexes; Lhermitte's sign; retrobulbar or optic neuritis; unsteadiness in walking; brain stem symptoms (diplopia, vertigo, vomiting); disorders of micturition; hemiplegia; trigeminal neuralgia; other pain syndromes; nystagmus and ataxia; cerebellar-type ataxia; Charcot's triad; diplopia; bilateral internuclear ophthalmoplegia; myokymia or paralysis of facial muscles; deafness; tinnitus; unformed auditory hallucinations (because of involvement cochlear connections); vertigo and vomiting (vestibular connections); transient facial anesthesia or of trigeminal neuralgia; bladder dysfunction; euphoria; depression; dementia, dull, aching pain in the low back; sharp, burning, poorly localized pains in a limb or both legs and girdle pains; abrupt attacks of neurologic deficit; dysarthria and ataxia; paroxysmal pain and dysesthesia in a limb; flashing lights; paroxysmal itching; and/or tonic seizures, taking the form of flexion (dystonic) spasm of the hand, wrist, and elbow with extension of the lower limb. A patient having MS may have one or more of these symptoms or other clinical manifestations typically associated with MS and one or more can be ameliorated by administrating of compounds according to the present invention.

The administration of Type IV phosphodiesterase inhibitors such as Rolipram can also block or reduce the physiological and pathogenic deterioration associated with MS, e.g., inflammatory response in the brain and other regions of the nervous system, breakdown or disruption of the bloodbrain barrier, appearance of lesions in the brain, tissue destruction, demyelination, autoimmune inflammatory response, acute or chronic inflammatory response, neuronal death, and/or neuroglia death.

The active agents of this invention, e.g., Rolipram, are useful to treat the different types of MS, including the multifocal, CNS, relapsing and remitting course; the multifocal, CNS, progressive course; the single-site, relapsing and remitting course; and other variants of multiple sclerosis. See, e.g., Cecil's Textbook of Medicine, edited by James B. Wyngaarden, 1988.

Effects of the administration of Rolipram and other Type IV phosphodiesterase inhibitors include, e.g., preventing the disease, ameliorating symptoms of the disease, reducing the annual exacerbation rate (i.e., reducing the number of episodes per year), slowing the progression of the disease, or reducing the appearance of brain lesions (e.g., as identified by MRI scan). The episodic recurrence of the mentioned diseases such as MS can be ameliorated, e.g., by decreasing the severity of the symptoms (such as the symptoms described above) associated with the, e.g., MS episode, or by lengthening the time period between the occurrence of episodes, e.g., by days, weeks, months, or years, where the episodes can be characterized by the flare-up and exacerbation of disease symptoms, or preventing or slowing the appearance of brain inflammatory lesions. See, e.g., Adams, R. D., Principles of Neurology, 1993, page 777, for a description of a neurological inflammatory lesion.

Other specific, suitable, non-limiting examples of Type IV phosphodiesterase inhibitors which can be employed in this invention include compounds described in WO93/19068, compounds RO 20-1724 (4-[(3-butyoxy-4-methoxyphenyl)methyl]-2-imidazolidinone), ICI 63197 (2-amino-6-methyl-4-propyl[1,2,4]triazolo[1,5-a]pyrimindin-5(4H)-one), denbufylline and etazolate.

By "Type IV phosphodiesterase inhibitor", "specific Type IV phosphodiesterase inhibitor", and similar expressions are meant a selective, i.e., specific, such inhibitor, where the compound binds to or inhibits preferentially the Type IV phosphodiesterase when compared to known types of phosphodiesterase types, e.g., I, II, or III, e.g., whereby the compound has a lower $IC_{50}$ (more potent) for the Type IV phosphodiesterase, such as where the $IC_{50}$ is, e.g., 2-fold, 5-fold, 10-fold, 50-fold, or more potent, for the Type IV phosphodiesterase compared to another known type of phosphodiesterase, e.g., I, II, or III. Such selectivity of a compound according to the present invention for a Type IV phosphodiesterase can also be conferred by other means, such as the manner in which it is delivered to its target, e.g., the compound can be associated with an agent which targets it to a specific tissue or cell type having the Type IV phosphodiesterase; the manner in which it interacts with the host's metabolism and/or physiology; or synthesizing PDE inhibitor prodrugs where activation of the PDE inhibitor is accomplished by enzymes present in the desired cells or tissues but absent in others.

The specific inhibition of a Type IV phosphodiesterase can be measured conventionally, e.g., according to the methods described in Reeves et al., Biochem. J., 241:535–541, 1977; by macrophage assay, as described, e.g., in Schade et al., Europ. J. Pharmacol., 230:9–14, 1993; or WO 93/19068. For a review of phosphodiesterase specificity and how to determine it, see, e.g., Nicholson et al., Trends Pharmacol. Sci., 12:19–27 (1991).

The activity of this invention of Type IV phosphodiesterase inhibitors such as Rolipram can be detected, for example, in animals suffering from Experimental Allergic Encephalmyelitis (EAE), an experimental T-lymphocyte initiated disease of the CNS. It can be produced, e.g., in rodents, guinea pigs, rabbits, and primates, by, e.g., immunizing animals with myelin, e.g., from a human brain, and/or corticosteroid administration over a long period of time. It can also be produced by injecting an animal with T-lymphocytes obtained from an animal suffering from EAE.

In particular, the activity can be detected in Callithrix jacchus (common marmoset) which has been immunized with myelin, e.g., from a human brain. The Callithrix jacchus develops EAE with essentially similar histopathology and neurological symptoms as those at certain stages of the human disease, MS.

The pharmaceutical compositions according to the present invention are prepared conventionally, comprising substances which are customarily used in pharmaceuticals, e.g., see Remington's Pharmaceutical Sciences, 18th ed., Mack Publishing Company (1990), including excipients, carriers, adjuvants and buffers. The compositions can be administered, e.g., parenterally, enterally, orally, intramuscularly, topically, subcutaneously, intravenously, by aerosol, intrathecally directly into the cerebral spinal fluid of the CNS, or preferably by sustained release using, e.g., an implanted mini-osmotic pump (e.g., the ALZET pump manufactured by ALZA Corporation, P. O. Box 10950, Palo Alto, Calif. 94303), or other routes useful to achieve an effect.

Conventional excipients include pharmaceutically acceptable organic or inorganic carrier substances suitable for parenteral, enteral or topical application which do not deleteriously react with the agents. Suitable pharmaceutically acceptable adjuvants include, but are not limited to, water, salt solutions, alcohols, gum arabic, vegetable oils, polyethylene glycols, gelatine, lactose, amylose, magnesium stearate, talc, silicic acid, viscous paraffin, perfume oil, fatty acid monoglycerides and diglycerides, pentaerythritol fatty acid esters, hydroxy-methylcellulose, polyvinyl pyrrolidone, cyclodextrins, etc. The pharmaceutical preparations can be sterilized and, if desired, mixed with stabilizers, wetting agents, emulsifiers, salts for influencing osmotic pressure, buffers, coloring, flavoring and/or aromatic substances, etc., which do not react deleteriously with the active compounds.

For parenteral application, particularly suitable are injectable sterile solutions, preferably oil or aqueous solutions, as well as suspensions, emulsions or implants, including suppositories. Ampoules are convenient unit dosages.

For enteral application, particularly suitable are tablets, dragees, suppositories or capsules having talc and/or a carbohydrate carrier or binder. The carrier may be lactose, corn starch, potato starch or a combination thereof. A syrup or elixir may be used when a sweetened vehicle is employed.

The compositions can also be formulated in an aqueous solution, optionally with the addition of additives customary in galenicals, for example, buffers; electrolytes such as sodium chloride; antioxidants such as ascorbic acid; adjuvants, e.g., methyl cellulose, lactose and mannitol and/or surfactants, e.g., lecithins and Tweens and/or aromatic substances for flavoring, e.g., ethereal oils.

The pharmaceutical compositions of the present invention can also comprise other active agents.

The dosage of the pharmaceutical composition can vary according to, e.g., the manner of administration, the disease being treated and its severity, the overall health and condition of the patient, the age of the patient or other usual criteria. Total dosages of phosphodiesterase inhibitors for all uses mentioned herein typically are from about 0.01 mg/kg to about 2.0 mg/kg per day, preferably 0.1 mg/kg to 0.7 mg/kg per day, more preferably, 0.5 mg/kg/day. Analogous amounts of other Type IV phosphodiesterase inhibitors can be determined routinely based on the information given herein, e.g., using the EAE model. However, any amount which is effective in treating MS can be administered to ameliorate or treat the disease. Dosages are determined conventionally, see, e.g., Remington's Pharmaceutical Sciences, 18th ed., Mack Publishing Company (1990). The composition may be administered in a single dose unit or in multiple dosages administered, e.g., twice, three, or four times a day, or by an osmotic pump, which delivers the drug(s) continuously.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever.

In the foregoing and in the following examples, all temperatures are set forth uncorrected in degrees Celsius; and, unless otherwise indicated, all parts and percentages are by weight.

The entire disclosures of all applications, patents, and publications cited herein are hereby incorporated reference.

EXAMPLES

Rolipram was produced by Schering AG (Berlin) and is comprised of (+) and (−) racemates of 4-[(3-cyclopentyloxy)-4-methoxyphenyl]-2-pyrrolidinone. It was dissolved in dimethylsulfoxide (DMSO) at 20 mg/ml.

Human brain white matter homogenate was prepared from autopsy material in complete Freund's adjuvant (CFA) containing *M. tuberculosis* (strain H37 Ra).

*Bordetella pertussis* vaccine was obtained from the Massachusetts Public Health Department, Biological Laboratories, Boston, Mass.

Zofran was obtained from the University of California Medical Center Pharmacy.

The marmosets were purchased from the New England Regional Primate Research Center and were maintained and cared for in accordance with the guidelines of the Internal Animal Care and Use Committee of the University of California, San Francisco.

Animals were immunized with human brain white matter homogenate (200 mg) in CFA containing 3 mg/ml killed *M. tuberculosis* (H37 Ra strain) by intradermal injection (0.6 ml) over four sites on the doral axilla and inguinal region. On the day of immunization and again 2 days later $10 \times 10^{10}$ inactivated *Bordetella pertussis* (*Bordetella pertussis* vaccine) were infused intravenously in 10 ml saline.

On day 5, following immunization, animals were injected subcutaneously in the back of the neck with DMSO (placebo) or with DMSO containing Rolipram to give a dose of 10 mg/kg. Treatment with DMSO or DMSO with Rolipram was preceded 20 min. by an injection of 0.3–0.6 mg/kg Zofran intramuscularly (Odansetron Hydrochloride, Glaxo) to prevent salivation, vomiting, excessive grooming, and head twists. Such treatments were repeated every 48 hours throughout the study.

Animals were observed daily and subjected to a standardized scoring system to record the severity of clinical symptoms:

0. Normal
1. Lethargy, anorexia, weight loss
2. Ataxia, tremor
3. Blindness, paraplegia or hemiplegia
4. Quadraparesis or quadriplegia
5. Moribund At various times, animals were anesthetized and subjected to MRI.

EXPERIMENT 1

Prevention of EAE by Rolipram Treatment

Marmosets were immunized with spinal cord homogenate as described. On day 5, following immunization, three marmosets received Rolipram (10 mg/kg) in DMSO. See FIG. 1, A, B, and C. Two marmosets received an equivalent volume of DMSO after the same interval. See FIG. 1, D and E. The treatment was repeated every 48 hours.

The animals treated with DMSO (placebo) developed clinical symptoms consistent with EAE 15 days following immunization; see FIG. 1, D and E. None of the Rolipram treated animals developed symptoms during the 8 week interval of observation; see FIG. 1, A, B, and C.

Magnetic Resonance Imaging (MRI) analysis showed that the two animals with EAE symptoms developed one or more lesions in the brain which "enhanced" with Magnevist (gadolinium, DTPA), indicating an active edematous response consistent with the vascular inflammatory lesions seen in EAE or MS (Alvord, etc.). None of the Rolipram treated animals developed detectable lesions during the 8 week interval of observation.

Development of EAE After Withdrawal of Rolipram

On day 60, following immunization, the treated animals were removed from treatment and observed for signs of EAE. Two marmosets began to show clinical signs of EAE on day 17, following withdrawal of Rolipram.

EXPERIMENT 2

Treatment of Active EAE with Rolipram

Figure 2:
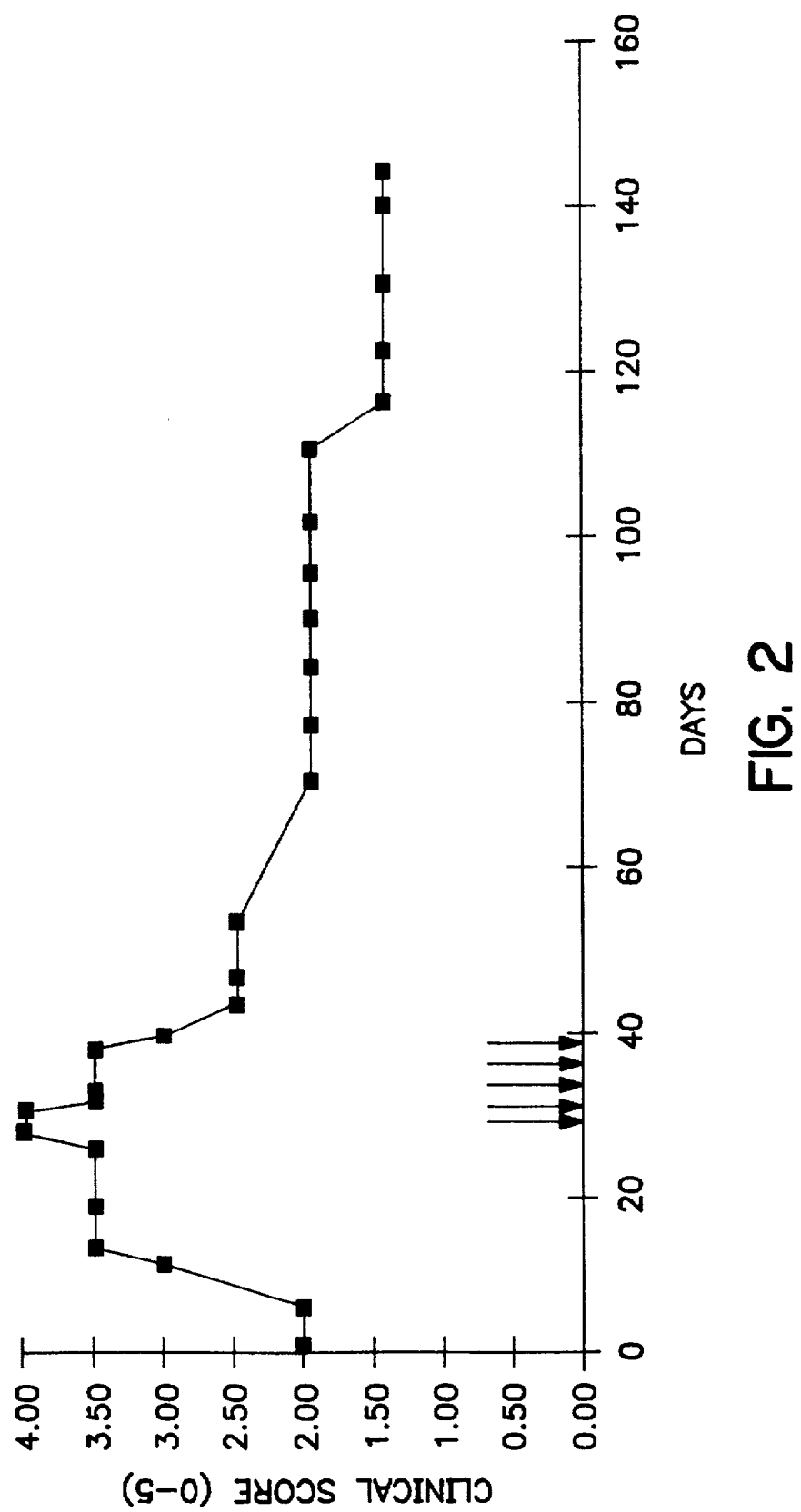
FIG. 2 shows the treatment with Rolipram of marmoset having EAE.

In the previous experiment, it was clearly demonstrated that Rolipram could prevent EAE. It is of interest to determine if Rolipram can also affect active EAE. In this experiment, a marmoset was immunized as previously described, allowed to develop symptoms of chronic EAE and subsequently treated with Rolipram. The animal was treated with escalating doses of Rolipram in DMSO administered as described in the previous experiment. The physical symptoms were monitored as described and MRI analysis was done at times before and after treating (FIG. 2).

The animal showed marked improvement on day 10 after initiating treatment. The animal showed MRI improvement on day 14 following initiating Rolipram treatment and, from that time, the condition stabilized with slower improvements.

The results of Experiment 1 indicate that Rolipram treatment blocked the neurological signs of EAE. The MRI results indicate that the inflammatory response was blocked and demyelination did not occur. The untreated control animals developed clear signs of EAE and inflammatory lesions as indicated by MRI analysis. The fact that treated animals developed EAE when removed from treatment showed that the immune response to brain homogenate had occurred sufficiently to initiate the disease; however, some subsequent step in pathogenesis was blocked.

The results of Experiment 2 indicate that Rolipram treatment can inhibit active disease.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

We claim:

1. A method of treating multiple sclerosis, comprising administering to a host in need thereof an effective amount of a compound according to formula I

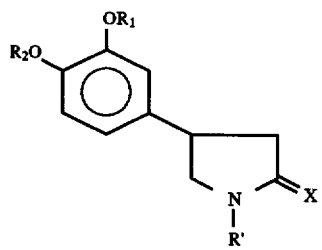

wherein:

$R_1$ and $R_2$ each are alike or different and are $C_{1-18}$-alkyl with at least one being other than methyl, a heterocyclic ring, or $C_{1-5}$-alkyl substituted by one or more of halogen atoms, hydroxy, carboxy, alkoxy, alkoxycarbonyl or an amino group;

R' is a hydrogen atom, alkyl, aryl or acyl; and X is an oxygen atom or a sulfur atom.

2. A method of claim 1, wherein said compound is 4-[(3-cyclopentyloxy)-4-methoxyphenyl]-2-pyrrolidinone.

3. A method according to claim 1, wherein one of $R_1$ and $R_2$ is methyl, and the other is $C_{3-7}$-cycloalkyl.

4. A method according to claim 1, wherein one of $R_1$ and $R_2$ is methyl and the other is $C_{3-7}$-cycloalkyl, R' is H, and X is O.

5. A method of claim 1, wherein the time between or the severity of symptoms of episodic recurrences of multiple sclerosis is ameliorated.

6. A method according to claim 1, wherein an inflammatory lesion associated with said multiple sclerosis is prevented or treated.

7. A method according to claim 1, wherein the appearance of an inflammatory lesion associated with said multiple sclerosis is slowed.

8. A method according to claim 1, wherein said compound is a Type IV phosphodiesterase.

9. A method according to claim 1, wherein said compound is administered by an implanted osmotic pump.

10. A method of claim 2, wherein the host is human.

11. A method of claim 10, wherein the multiple sclerosis is relapsing and remitting.

12. A method of claim 10, wherein the multiple sclerosis is the multifocal CNS, relapsing and remitting course; the multifocal CNS, progressive course; or the single-site, relapsing and remitting course.

13. A method of treating multiple sclerosis comprising administering to a host in need thereof an effective amount of a Type IV phosphodiesterase inhibitor.

14. A method according to claim 13, wherein the time between or the severity of symptoms of the episodic recurrences of the multiple sclerosis is ameliorated.

15. A method according to claim 13, wherein an inflammatory lesion associated with said multiple sclerosis is treated.

16. A method according to claim 13, wherein the appearance of an inflammatory lesion associated with said multiple sclerosis is slowed.

17. A method of treating multiple sclerosis comprising administering to a human in need thereof an effective amount of 4-[(3-cyclopentyloxy)-4-methoxyphenyl]-2-pyrrolidinone.

18. A method according to claim 17, wherein the time between or the severity of symptoms of the episodic recurrences of the multiple sclerosis is ameliorated.

19. A method according to claim 17, wherein an inflammatory lesion associated with said multiple sclerosis is treated.

20. A method of claim 17, wherein the multiple sclerosis is relapsing and remitting.

21. A method of claim 17, wherein the multiple sclerosis is the multifocal CNS, relapsing and remitting course; the multifocal CNS, progressive course; or the single-site, relapsing and remitting course.

22. A method of claim 17, wherein the multiple sclerosis is neuromyelitis optica, diffuse sclerosis, transitional sclerosis, acute disseminated encephalomyelitis, or optic neuritis.

23. A method of claim 17, wherein 0.01 mg/kg–2.0 mg/kg per day of 4-[(3-cyclopentyloxy)-4-methoxyphenyl]-2-pyrrolidinone is administered.

24. A method of claim 17, wherein 0.1 mg/kg–0.7 mg/kg per day of 4-[(3-cyclopentyloxy)-4-methoxyphenyl]-2-pyrrolidinone is administered.

25. A method of claim 17, wherein the effective amount is administered as a single dose.

26. A method of claim 17, wherein the effective amount is administered in multiple doses.

27. A method of claim 17, wherein 4-[(3-cyclopentyloxy)-4-methoxyphenyl]-2pyrrolidinone is administered intramuscularly, subcutaneously, intravenously, or intrathecally.

28. A method of claim 17, wherein 4-[(3-cyclopentyloxy)-4-methoxyphenyl]-2-pyrrolidinone is administered by sustained release.

29. A method of claim 28, wherein the sustained release is by an implanted osmotic pump.

30. A method of claim 17, wherein the ongoing immune response or autoimmune response associated with the disease is suppressed.

31. A method of claim 17, wherein the appearance of a brain lesion is reduced as identified by a MRI scan.

32. A method of preventing the recurrence of or treating multiple sclerosis, comprising administering to a host in need thereof an effective amount of a compound according to formula I

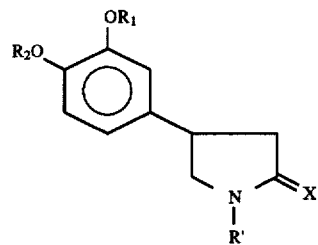

wherein:
R$_1$ and R$_2$ each are alike or different and are C$_{1-18}$-alkyl with at least one being other than methyl, a heterocyclic ring, or C$_{1-5}$-alkyl substituted by one or more of halogen atoms, hydroxy, carboxy, alkoxy, alkoxycarbonyl or an amino group;
R' is a hydrogen atom, alkyl, aryl or acyl; and X is an oxygen atom or a sulfur atom.

* * * * *

UNITED STATES PATENT AND TRADEMARK OFFICE
CERTIFICATE OF CORRECTION

PATENT NO. : 5,672,622
DATED : September 30, 1997
INVENTOR(S) : Joel Hedgpeth et al.

It is certified that error appears in the above-identified patent and that said Letters Patent is hereby corrected as shown below:

Title Page, item [75] inventors: and item [19]

Delete "Joseph" and replace with - - Joel - -. Change "Hedgepeth" to read - - Hedgpeth - -.

Signed and Sealed this

Fifth Day of May, 1998

*Attest:*

BRUCE LEHMAN

*Attesting Officer*      *Commissioner of Patents and Trademarks*